US012653479B2

(12) United States Patent
Liu et al.

(10) Patent No.: US 12,653,479 B2
(45) Date of Patent: Jun. 16, 2026

(54) CONTROLLING A COMPUTED TOMOGRAPHY IMAGING PROCEDURE

(71) Applicant: KONINKLIJKE PHILIPS N.V., Eindhoven (NL)

(72) Inventors: Jinling Liu, Solon, OH (US); Ravindra Mohan Manjeshwar, Solon, OH (US); Steven J. Utrup, Willoughby, OH (US); Gad Yehuda Wolach, Highland Heights, OH (US); Hao H Wang, Shenyang (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 156 days.

(21) Appl. No.: 18/684,204

(22) PCT Filed: Aug. 15, 2022

(86) PCT No.: PCT/EP2022/072765
§ 371 (c)(1),
(2) Date: Feb. 16, 2024

(87) PCT Pub. No.: WO2023/020995
PCT Pub. Date: Feb. 23, 2023

(65) Prior Publication Data
US 2024/0358341 A1 Oct. 31, 2024

(30) Foreign Application Priority Data

Aug. 18, 2021 (WO) ................ PCT/CN2021/113285
Sep. 13, 2021 (EP) ..................................... 21196236

(51) Int. Cl.
*A61B 6/00* (2024.01)
*A61B 6/03* (2006.01)
*A61B 6/06* (2006.01)

(52) U.S. Cl.
CPC ................ *A61B 6/54* (2013.01); *A61B 6/032* (2013.01); *A61B 6/06* (2013.01)

(58) Field of Classification Search
CPC ....... A61B 6/032; A61B 6/0487; A61B 6/027; A61B 6/54; A61B 6/06; A61B 6/542;
(Continued)

(56) References Cited

U.S. PATENT DOCUMENTS

| | | | |
|---|---|---|---|
| 5,539,796 A * | 7/1996 | Takagi | A61B 6/032 |
| | | | 378/20 |
| 7,968,853 B2 | 6/2011 | Altman | |
| 2006/0039536 A1 | 2/2006 | Nishide | |
| 2006/0177002 A1 | 8/2006 | Toth | |

(Continued)

FOREIGN PATENT DOCUMENTS

| | | |
|---|---|---|
| JP | U465512 | 6/1992 |
| JP | 2009142518 A | 7/2009 |

(Continued)

OTHER PUBLICATIONS

PCT International Search Report, International application No. PCT/EP2022/072765, Nov. 25, 2022.

*Primary Examiner* — Irakli Kiknadze
(74) *Attorney, Agent, or Firm* — Larry Liberchuk

(57) ABSTRACT

A mechanism for controlling the operation of a CT scanner during a scanning procedure. A radiation outputting system is configured to output radiation during an imaging phase of the scanning procedure. The subject support (patient table) of the CT scanner is controlled to move linearly, e.g. according to some predetermined linear pattern, during this imaging phase. The linear movement of the subject support includes at least one acceleration and/or deceleration phase. At least a beam width of radiation output by the CT scanner is controlled throughout the imaging phase responsive to the speed of the subject support.

13 Claims, 4 Drawing Sheets

(58) Field of Classification Search
CPC ......... A61B 6/4452; A61B 6/51; A61B 6/469;
A61B 6/00; A61B 6/42; A61B 6/52;
A61B 6/4435; A61B 6/405; A61B
6/5258; A61B 6/4035; A61B 6/512; A61B
6/04; A61B 8/0875; A61B 6/547; A61B
6/0457; A61B 6/4014; A61B 6/4085;
A61B 6/482; A61B 6/4291; A61B 5/026;
A61B 6/5205; A61B 6/488; A61B 6/541;
A61B 6/504; A61B 5/352; A61B 6/583;
A61B 5/0456; G01N 23/046; G01N
23/04; G01N 2223/419; G01N 2223/612;
G21K 1/04; G06T 12/30; G06T 11/006;
G06T 2211/421; G06T 2211/416
USPC ................................................ 378/4, 19, 62
See application file for complete search history.

(56) References Cited

U.S. PATENT DOCUMENTS

| | | |
|---|---|---|
| 2007/0110211 A1 | 5/2007 | Hsieh |
| 2010/0310040 A1 | 12/2010 | Hsieh |
| 2013/0251101 A1 | 9/2013 | Saito |
| 2015/0043708 A1 | 2/2015 | Allmendinger |

FOREIGN PATENT DOCUMENTS

| | | |
|---|---|---|
| JP | 2012161680 A | 8/2012 |
| JP | 2016161680 A | 8/2012 |
| JP | 2017035203 A | 2/2017 |
| JP | 2019111190 A | 7/2019 |
| WO | WO2010047380 A1 | 4/2010 |
| WO | WO2014037253 A1 | 3/2014 |

* cited by examiner

100

102

200

CONTROLLING A COMPUTED TOMOGRAPHY IMAGING PROCEDURE

FIELD OF THE INVENTION

The present invention relates to the field of medical imaging, and in particular to the field of computed tomography imaging.

BACKGROUND OF THE INVENTION

A computed tomography (CT) scanner is a common piece of equipment in modern medical imaging. Generally, a CT scanner is formed of a generally stationary portion and a rotating portion. The rotating portion supports a radiation outputting system such as an X-ray tube and an opposing radiation measurement system that generates raw data that can be used to reconstruct the CT image(s). A subject support supports an object/subject in an examination region around which the rotating portion rotates. During a scanning procedure, the subject support moves linearly to facilitate imaging of different sections of the supported subject/object.

One mode of operation for a CT scanner is a helical or spiral mode, in which the subject support is accelerated to move at a predefined (and constant) speed relative to the gantry rotation speed to acquire the needed raw data to reconstruct CT images.

This relationship between the moving speed (V) of the subject support and the gantry rotation speed is defined by CT scan pitch, which is the table distance travelled in one 360° ($2\pi$) gantry rotation divided by the total thickness of all simultaneously acquired slices during that rotation.

When performing a helical/spiral mode scan (or simply "helical CT scan"), there is a period of time during which the subject support accelerates or decelerates, e.g. to reach the predefined speed or to reach standstill after travelling at the predefined speed. Conventionally, no imaging is performed during this acceleration/deceleration phase, such that part of the subject/object, which could be theoretically imaged, are not imaged in practice. In current CT scanners, an over-scan region is added before the prescribed scan region and another over-scan region is added after the prescribed scan region for reconstruction of the helical scan images. The additional pre and post regions increase the region of the subject exposed to x-ray radiation. Also in current CT scanners, while the collimator is open, the x-ray tube is turned on before raw data acquisition starts to ensure the tube stabilizes when data acquisition starts, which also introduces extra radiation to the subject being scanned.

SUMMARY OF THE INVENTION

The invention is defined by the claims.

According to examples in accordance with an aspect of the invention, there is provided a computer-implemented method of operating a computed tomography scanner comprising a subject support configured to move linearly and a rotating portion that mounts a radiation outputting system and controllably rotates around the subject support.

The computer-implemented method comprises performing a scanning procedure comprising: controlling the radiation outputting system to output radiation during/throughout an imaging phase of the scanning procedure; controlling the subject support to move linearly, the linear movement of the subject support during/throughout the imaging phase of the scanning procedure including at least one acceleration or deceleration phase; and controlling one or more parameters of the computed tomography scanner responsive to the speed of the subject support, wherein the one or more parameters comprises at least a beam width of the radiation output by the radiation outputting system.

The present disclosure thereby provides a mechanism for controlling the operation of a CT scanner, e.g. during a helical scanning procedure. During a helical scanning procedure, a rotating portion rotates as the subject support is moved linearly.

The present invention proposes to control beam width of radiation provided by a radiation outputting system out of the collimator responsive to the speed of the (linearly moving) subject support. This facilitates control over the amount of radiation exposed (dose) on/to a subject positioned on the subject support. In particular, it is recognized that appropriate control over this characteristic of the radiation facilitates provision of a constant dose of radiation to all parts of a subject positioned on the subject support.

Conceptually, a prescribed image region is divisible into one or more acceleration regions, constant speed regions, and deceleration regions, the sum of which equals the total prescribed image region. By controlling the beam width responsive to patient table speed, imaging can be performed during each of these regions without needing to add extra pre and post scan regions on top of the prescribed image region. The beam width is preferably controlled in such a way that a dose provided to the subject will remain constant throughout these regions.

The skilled person will appreciate that the CT scanner may comprise a number of other features or elements, e.g. a radiation measurement system, a control panel, a console and so on.

These are not specified in the claim set for the sake of conciseness, and because they are well known elements of a standard CT scanner.

Optionally, the step of controlling one or more parameters of the computed tomography scanner responsive to the speed of the subject support comprises controlling the beam width proportionally to the speed of the subject support.

The radiation output by the radiation outputting system is the radiation incident within an examination region, e.g. the radiation that will interact with the subject support. In particular, if a patient/subject occupies an entire surface of the subject support, then radiation output by the radiation outputting system will interact with the subject support.

In some examples, the radiation outputting system comprises a radiation source configured to generate radiation and a collimator configured to control the beam width of radiation generated by the radiation source; and the step of controlling the one or more parameters of the computed tomography scanner comprises controlling the beam width by controlling an operation of the collimator.

Using a collimator to control a beam width provides a highly sensitive and accurate mechanism to control the beam width of the radiation output by the radiation outputting system. This approach facilitates direct control over the area of radiation incident upon a subject positioned on the subject support.

The collimator may comprise a collimator opening having a controllable width, and the step of controlling the beam width comprises controlling a width of the collimator opening responsive to the speed of the subject support.

In some examples, the width of the collimator opening is defined by a distance between a front blade and a rear blade aligned in a direction of travel of the subject support, and the step of controlling a width of the collimator opening comprises controlling the distance between the front blade and the rear blade.

In at least one embodiment, wherein the step of controlling one or more parameters of the computed tomography scanner comprises setting and maintaining the beam width to be equal to 0 until the radiation generated by the radiation source has stabilized. In other words, the beam width may be set and maintained at zero whilst the radiation source is turned on and/or is stabilizing. Thus, the step of controlling the radiation outputting system to output radiation may comprise a step of controlling the radiation source to begin generating radiation (whilst the controlling of the parameters keeps the beam width at 0, i.e. the collimator shut). Once the radiation source has stabilized, allowing the beam width to have a width greater than 0 (i.e. allow the collimator to open) for raw data acquisition.

In some examples, the subject support does not begin moving until the radiation source has stabilized and the beam width is permitted to have a width greater than 0. Thus, the step of controlling the subject support to move linearly may comprise controlling the subject support to move linearly only after the radiation source has stabilized.

Mechanisms for identifying when the radiation source has stabilized will be readily apparent to the skilled person, e.g. by waiting a predetermined period of time after powering the radiation source (e.g. according to known times for the radiation source to stabilize).

The present invention facilitates control over the beam width during the stabilization of the source of the scanning procedure. The proposed approach of maintain the beam width at 0 until the radiation source has stabilized reduces (unnecessary) radiation exposure or dosage of a subject positioned on the subject support. In particular, beam width will be kept at 0 and imaging (i.e. measuring of output radiation) will not take place whilst the source is stabilizing.

In some examples, the step of controlling the one or more parameters of the computed tomography scanner comprises controlling the one or more parameters such that a total radiation dosage per volume of a subject positioned on the subject support remains substantially constant throughout the scanning procedure.

Optionally, the step of controlling one or more parameters of the computed tomography scanner comprises controlling the one or more parameters of the computed tomography scanner so that a CT scan pitch is constant throughout the scanning procedure.

In at least one embodiment, the step of controlling one or more parameters of the computed tomography scanner comprises controlling the beam width to be equal to the product of the speed of the subject support and the time taken for the rotating portion to perform a $2\pi$ rotation, divided by a desired CT scan pitch.

The one or more parameters of the computed tomography scanner may further comprise an intensity of the radiation output by the radiation outputting system. In some examples, the radiation outputting system comprises an X-ray tube and the step of controlling an amount of radiation intensity output by the radiation outputting system comprises controlling an emission current supplied to the X-ray tube.

The one or more parameters of the computed tomography scanner may further comprise a rotation speed of the rotating portion of the computed tomography scanner.

The step of controlling the subject support to move linearly may comprise controlling the subject support to have a linear movement including a single acceleration and/or a single deceleration phase.

The scanning procedure may comprise obtaining (during/throughout the imaging phase of the scanning procedure) using a radiation measurement system mounted on the rotating portion, raw signal data responsive to the absorption of radiation output by the radiation outputting system by a subject positioned on the subject support.

There is also proposed a computer program product comprising computer program code means which, when executed on a computing device having a processing system, cause the processing system to perform all of the steps of any herein described method. The computer program product may be formed of a (non-transitory) computer-readable medium.

There is also proposed a processing system configured to operate a computed tomography scanner comprising a subject support configured to move linearly and a rotating portion that mounts a radiation outputting system and controllably rotates around the subject support, the processing system being configured to control a scanning procedure comprising: controlling the radiation outputting system to output radiation during/throughout an imaging phase of the scanning procedure; controlling the subject support to move linearly, the linear movement of the subject support during/throughout the imaging phase of the scanning procedure including at least one acceleration or deceleration phase; and controlling one or more parameters of the computed tomography scanner responsive to the speed of the subject support, wherein the one or more parameters comprises at least a beam width of the radiation output by the radiation outputting system.

There is also proposed an image generating system comprising the processing system and an image reconstruction system that is configured to process projection data, generated by a radiation measurement system of the computed tomography scanner, to reconstruct one or more 2D and/or 3D images.

There is also proposed an imaging system comprising: the projection system or the image generation system and the computed tomography scanner comprising the subject support configured to move linearly and the rotating portion that mounts the radiation outputting system and controllably rotates around the subject support. The computed tomography scanner may further comprise a radiation measurement system configured to generate projection data responsive to radiation incident on the radiation measurement system.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
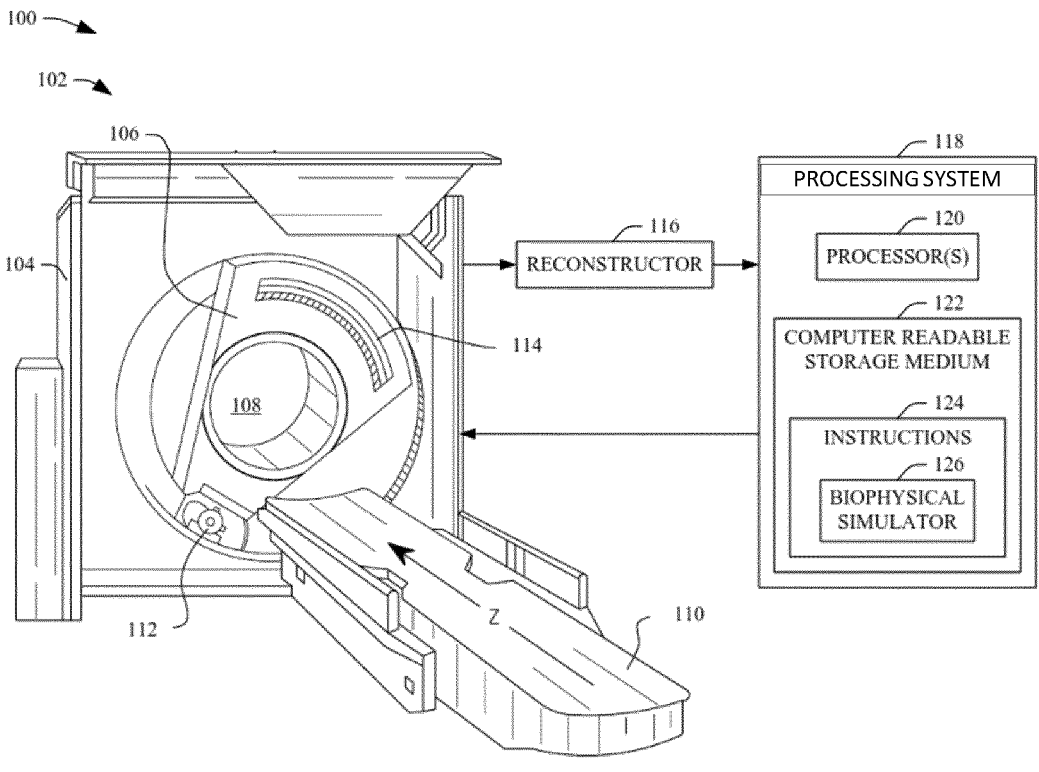
FIG. 1 illustrates a computed tomography scanner system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a mechanism for controlling the operation of a CT scanner during a scanning procedure. A radiation outputting system is configured to output radiation during an imaging phase of the scanning procedure. The subject support (patient table) of the CT scanner is controlled to move linearly, e.g. according to some predetermined linear pattern, during this imaging phase. The linear movement includes at least one acceleration and/or deceleration phase. At least a beam width of radiation output by the CT scanner is controlled throughout the imaging phase responsive to the speed of the subject support.

Embodiments are based on a realization that a CT scan pitch and/or amount of irradiation per unit volume of an examination region can be controlled by controlling a beam width. This facilitates maintenance of a constant pitch or irradiation per unit volume, or maintaining a pitch or irradiation per unit volume below some predetermined threshold, to control radiation exposure of the subject. This enables an imaging phase of the scanning procedure to include periods during which the subject support is accelerating and/or decelerating, increasing a size of an available region for imaging.

Embodiments can be employed in any suitable CT scanning system, which can be used in a wide variety of industries such as the healthcare industry, anthropology industries and/or archeological industries.

FIG. 1 schematically illustrates a computed tomography scanner system 100 including a computed tomography scanner. The computed tomography scanner 102 includes a generally stationary portion 104 and a rotating portion 106, which is rotatably supported by the stationary portion 104 and rotates around an examination region 108 about a z-axis. A subject support 110, such as a couch, supports an object or subject (e.g. a patient) in the examination region 108.

A radiation outputting system 112, comprising a radiation source (such as an x-ray tube) and a collimator, is rotatably supported by the rotating portion 106, rotates with the rotating portion 106, and outputs radiation that traverses the examination region 108.

A radiation measurement system 114, e.g. a radiation sensitive detector array, subtends an angular arc opposite the radiation source 112 across the examination region 108. The radiation measurement system ("radiation detector") detects radiation traversing the examination region 108 and generates an electrical signal(s) (projection data) indicative thereof.

The radiation measurement system 114 can include single layer detectors, direct conversion photon counting detectors, and/or multi-layer detectors. The direct conversion photon counting detectors may include a conversion material such as CdTe, CdZnTe, Si, Ge, GaAs, or other direct conversion material. An example of multi-layer detector includes a double decker detector such as the double decker detector described in U.S. Pat. No. 7,968,853 B2, filed Apr. 10, 2006, and entitled "Double Decker Detector for Spectral CT,".

A reconstructor 116 receives projection data from the radiation measurement system 114 and reconstructs one or more CT images from the projection data. The reconstructed CT images may comprise one or more 2D or 3D images. Mechanisms for reconstructing one or more CT images from projection data are well-established in the art.

A processing system 118 is configured to control an operation of the computed tomography scanner, and in particular to control the operation of the computed tomography scanner during a scanning procedure. Approaches for controlling the operation of the computed tomography scanner according to embodiments form the subject of this disclosure.

During a scanning procedure, the processing system 118 controls the subject support 110 to move linearly along the z-axis. The processing system 118 also controls the rotating portion 106 to rotate about the examination region 108 and the radiation outputting system 112 to output radiation into the examination region. As previously explained, the radiation measurement system 114 collects radiation traversing the examination region and generates projection data (e.g. as an electrical signal) indicative to radiation that has traversed the examination region. The reconstructor 116 then reconstructs a CT image from the projection data.

The processing system 118 may include a processor 120 (e.g., a microprocessor, a controller, a central processing unit, etc.) and a computer readable storage medium 122, which excludes non-transitory medium, and includes transitory medium such as a physical memory device, etc.

The computer readable storage medium 122 may include instructions 124 for controlling the operation of the computed tomography scanner. The processor 120 is configured to execute the instructions 124. The processor 120 may additionally be configured to execute one or more computer readable instructions carried by a carrier wave, a signal and/or other transitory medium. However, instead of a processor 120 executing instructions to perform a herein described method, the processor may instead comprise fixed-function circuitry (e.g. appropriately programmed field-programmable gate arrays (FPGAs) or the like) to carry out the described methods.

In some examples, the processing system may also serve as an operator console. The processing system 118 includes a human readable output device such as a monitor and an input device such as a keyboard, mouse, etc. Software resident on the processing system 118 allows the operator to interact with and/or operate the scanner 102 via a graphical user interface (GUI) or otherwise.

A processing system 118 may be configured to process CT images generated by the computed tomography scanner 102. This may, for instance, comprise controlling a user interface to display or provide a visual representation of reconstructed CT images.

As previously mentioned, the present disclosure proposes approaches for controlling the operation of the computed tomography scanner 102. In particular, the present disclosure proposes approaches for controlling the operation of the computed tomography scanner during the scanning procedure. These approaches may be carried out by the processing system 118.

Figure 2:
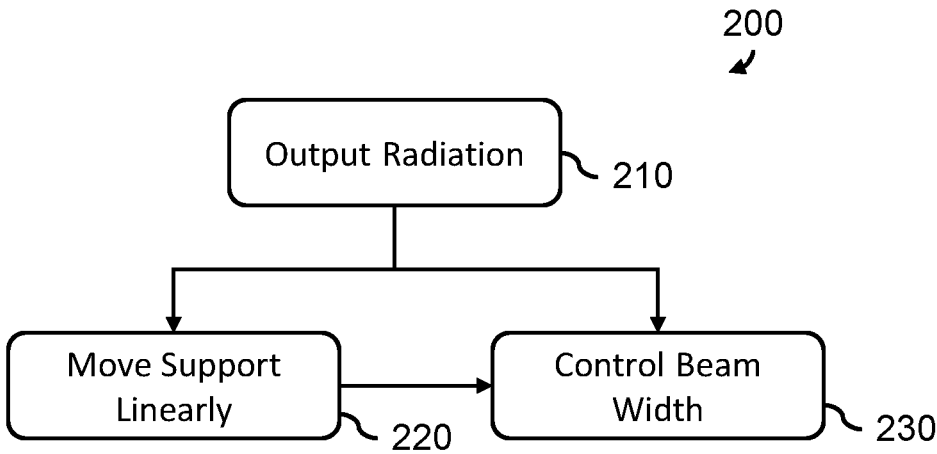
FIG. 2 illustrates a method according to an embodiment.

FIG. 2 is a flowchart illustrating a (computed-implemented) method 200 according to an embodiment. The computer-implemented method may be carried out by the processing system 118 of FIG. 1.

The method 200 is for operating a computed tomography (CT) scanner comprising a subject support configured to move linearly and a rotating portion (that mounts a radiation outputting system) and controllably rotates around the subject support. The CT scanner may further comprise a radiation measurement system configured to detect radiation output by the radiation outputting system (which may be at least partially absorbed by a subject positioned on the subject support).

The method 200 comprises a scanning procedure, which may be a helical scanning procedure. Generally, a scanning procedure can be divided into an "imaging phase" (during which projection data used to reconstruct image data, e.g. one or more 2D and/or 3D images, is generated) and a "non-imaging phase" (during which no projection data used to reconstruct image data, e.g. one or more 2D and/or 3D images, is generated). In a helical scanning procedure, the rotating portion rotates as the subject support moves linearly (e.g. so that the radiation output element and/or the radiation measurement system appear(s) to move in a spiral with respect to the subject support).

Steps for carrying out a scanning procedure are well known in the prior art, and may include additional steps that are not explicitly described in this disclosure for the sake of brevity. These steps include, but are not limited to, those previously described with reference to FIG. 1, e.g. using a radiation measurement system for detecting radiation output by the radiation outputting system and/or reconstructing images from projection data generated by a radiation measurement system.

The method 200 comprises a step 210 of controlling the radiation outputting system to output radiation during an imaging phase of the scanning procedure. In particular, the radiation outputting system outputs a non-zero radiation (to the examination region) throughout the imaging phase. Methods for controlling a radiation output system to output radiation are widely known and readily apparent to the skilled person, e.g. by supplying a current to an X-ray tube or the like.

As previously explained, an imaging phase is a phase during which radiation detected by a radiation measurement system of the CT scanner contributes to the generation of image data, e.g. one or more (2D or 3D) CT images, produced by the CT scanner. Thus, the scanning procedure (e.g. as part of step 210) may further comprise controlling the radiation measurement system to detect radiation output by the radiation outputting system.

The method 200 comprises a step 220 of controlling a linear motion of the subject support during the imaging phase of the computed tomography scanner to include at least one acceleration and/or a deceleration phase.

Thus, the linear motion may be controlled to have a single acceleration phase and/or a single deceleration phase. In another example, the linear motion may be controlled to have a plurality of acceleration phases and/or a plurality of deceleration phases. In some examples, the number of acceleration phases and the number of deceleration phases are equal. This later approach increases the overall size of the imaging area, as explained below.

Thus, the linear motion of the subject support is controlled according to some predetermined linear motion pattern, which defines a speed and direction of the linear motion. One example of a linear motion pattern would include (i.e. consist of) an acceleration phase, a steady state phase and a deceleration phase. However, other examples may include a plurality of different acceleration, steady state and/or deceleration phases. For instance, one linear motion pattern may comprise X acceleration phases, Y steady state phases and Z deceleration phases, e.g. where X=Z and Y=X−1.

It will be appreciated that the linear position of the subject support defines an area or volume of the examination region that is being irradiated by the radiation outputting system (when it is outputting radiation), and thereby a region of the examination area that is imaged (by detection of radiated radiation). Thus, there is a total imaging region, which is the entire region irradiated and imaged during the scanning procedure.

Figure 3:
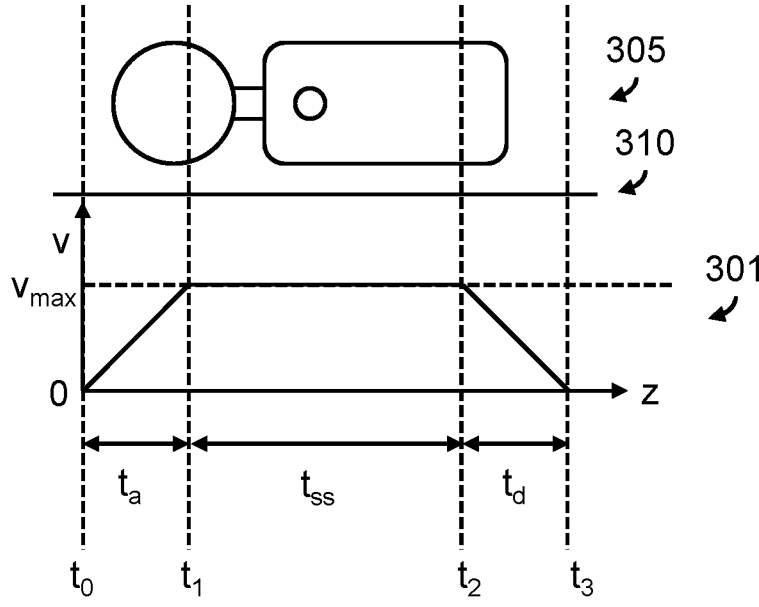
FIG. 3 illustrates an exemplary movement for a subject support during an imaging phase of a scanning procedure, for use in an embodiment.

FIG. 3 illustrates one example of a linear motion pattern 301 for the subject support. In particular, FIG. 3 illustrates a position (z) and a speed (v) of the subject support according to a linear motion pattern. FIG. 3 also illustrates a subject 305 positioned on a subject support 310, to demonstrate how the speed of the subject support can change with respect to a current position (of the rotating portion) with respect to the subject support.

The linear motion pattern comprises an acceleration phase $t_a$, a steady state phase $t_{ss}$ and a deceleration phase $t_a$. During the acceleration phase $t_a$, from time $t_0$ to time $t_1$, a speed of the subject support increases (from 0) to a maximum speed $V_{max}$. During the steady state phase $t_{ss}$, from time $t_1$ to time $t_2$, the speed of the subject support is held at the maximum speed $V_{max}$. During the deceleration phase, from time $t_2$ to time $t_3$, a speed of the subject support decreases to 0.

The maximum speed $V_{max}$ is not necessarily the maximum possible speed of the subject support, but rather the maximum speed for that linear motion pattern. This may be defined by a clinician, e.g. providing a user input, and will be bounded by the maximum possible speed of the subject support.

For the subject support being controlled according to the linear pattern illustrated by FIG. 3, and for linear acceleration (a) and deceleration (d), the subject support speed v(t) can be calculated as:

$$v(t) = \begin{cases} a \cdot t & t \leq t_1 \\ v_{max} & t_1 \leq t \leq t_2 \\ v_{max} - d \cdot (t - t_2) & t \geq t_2 \end{cases} \quad (1)$$

where:
  t: time during the scanning procedure, starting from to
  V: instant subject support speed at time t
  a: subject support acceleration
  d: subject support deceleration
  $V_{max}$: maximum subject support speed during steady state
  $t_1$: time acceleration phase ends
  $t_2$: time deceleration phase starts Turning back to FIG. 2, the method 200 also comprises a step 230 of controlling one or more (other) parameters of the computed tomography scanner responsive to the speed of the subject support. The one or more other parameters includes at least a beam width of radiation output by the radiation outputting element.

Thus, step 230 comprises controlling at least a beam width of radiation output by the radiation outputting element responsive to the speed of the subject support. Step 230 may also be performed throughout at least the imaging phase.

Other suitable parameters that might also be controlled in step 230 include a speed of rotation of the rotating portion and/or an intensity of radiation output by the radiation outputting element (and in particular, an intensity of radiation output by a radiation source of the radiation outputting element).

It is herein recognized that, for a conventional helical scanning procedure in which a speed of the rotating portion is constant, if radiation were output by the radiation outputting element during any acceleration and/or deceleration phases of the linear motion of the subject support, then the total amount of radiation per volume of the examination region during such phases would be greater than during the steady state phase. This is because the slower movement of the subject support during these phases causes a smaller gap or potentially a (greater) overlap between areas radiated between a $2\pi$ rotation of the rotating portion.

By way of further explanation, for the purposes of this disclosure, during a helical scanning procedures (for CT scanners), a "pitch" or CT scan pitch is defined as the total distance travelled by the subject support (along the z-axis) during one $2\pi$ rotation of the rotating portion, divided by the total thickness (along the z-axis) that is irradiated with radiation (i.e. the beam width of radiation output by the radiation outputting system).

In conventional imaging practices, if the subject were imaged throughout the entire movement of the subject support, the CT scan pitch would change over the course of the scanning procedure due to acceleration and deceleration of the subject support. This would affect the relative amount of radiation incident per volume of the examination region, and could lead to undesirable radiation dosing of a subject on the subject support.

To avoid this issue, conventional scanning procedures simply avoid imaging (e.g. avoid or minimize emitting radiation) during any acceleration or deceleration phases. This means that the total imaging area is limited to only the areas that can be irradiated whilst the linear motion of the subject support is in the steady state phase. In other words, the imaging phases of conventional scanning procedures do not include an acceleration or deceleration phases for the linear motion of the subject support.

The present disclosure proposes a different approach in which at least a beam width is controlled responsive to the speed of movement. This facilitates control over the size of the area/volume irradiated with radiation and therefore the total amount of radiation for each phase of the linear motion.

By adopting approaches according to the present disclosure, the size of the total imaging region can be effectively increased without impacting on the total amount of radiation (per volume irradiated area). In particular, the total imaging area can be increased to also include areas that can be irradiated whilst the linear motion of the subject support is in an acceleration and/or deceleration phase.

In other words, the imaging phase of a scanning procedure may be extended to include periods of acceleration/deceleration of the subject support, e.g. so that an imaging phase may occupy the entirety of the scanning procedure.

The relationship between pitch P(t), subject support speed v(t), rotation speed r(t) and beam width w(t) can be calculated as:

$$P(t) = \frac{v(t)}{w(t) \cdot r(t)} \quad (2)$$

The pitch P(t) is dimensionless, the subject support speed v(t) is in m/s (or mm/s), the rotation speed r(t) is in revolutions per second (RPS) and the beam width is in m (or mm). Generally, a beam width is a width of the beam of radiation at the isocenter of the rotating portion. The isocenter is an axis parallel with the z-axis and which passes through a center of the circle/cylinder around which the rotating portion rotates.

Thus, by controlling a beam width responsive to a change in subject support speed, a pitch of the scanning procedure can be controlled. In particular, by controlling a change in beam width to be proportional to a change in subject support speed, a maximum change in pitch during an acceleration/deceleration phase of the linear motion of the subject support can be reduced.

In particular examples, step 230 may be configured to comprise controlling only a beam width responsive to the speed of the subject support. In particular, step 230 may comprise controlling a beam width to maintain a constant pitch P (which may be predetermined, e.g. according to a user-input or scanning procedure). Suitable examples for a desired pitch value P are 0.5, 1, 2. Other pitch values are possible and known by those who are skilled in the art. By way of example, the pitch may be maintained to be a constant pitch having a value of between 0.5 and 2, e.g. between 0.5 and 1.5.

In this way, the step of controlling one or more parameters of the computed tomography scanner may comprise controlling the beam width to be equal to the product of the speed of the subject support and the time taken for the rotating portion to perform a $2\pi$ rotation (at its current speed), divided by a desired (CT scan) pitch.

This is equivalent to controlling the beam width to be equal to the speed of the subject support divided by the product of the desired (CT scan) pitch and the speed (in rotations per second) of the rotating portion of the CT scanner.

By way of example only, consider a scenario in which a desired pitch value P is 1, a rotation speed r is fixed at 5 rotations per second, a maximum speed $V_{max}$ for the subject support (i.e. a speed during the steady state phase of the linear motion) is 400 mm/s and an acceleration a is a constant value of 200 mm/s$^2$.

In this scenario, the acceleration phase will be 2 seconds long, in which the speed linearly increases from 0 to 400 mm/s. If step 230 comprises controlling a beam width to maintain a constant pitch (following equation (2)), then the beam width will also linearly increase from 0 to 80 mm. It will be apparent that, in this example, the magnitude of the beam width is thereby controlled to be proportional to the subject support speed.

In other examples, step 230 may be configured to comprise controlling a plurality of parameters of the computed tomography scanner, wherein the parameters include at least a beam width. The parameters may also include a rotation speed of the rotating portion and/or an intensity of radiation output by the radiation outputting element.

Equation (2) demonstrates how a pitch is also dependent upon the time taken for the rotating portion to perform a rotation, i.e. the speed of rotation. By controlling the speed of the rotating portion, a time taken for the rotating portion to perform a rotation can be changed, and therefore provides a further possible controllable variable for controlling the pitch of the scanning procedure.

In some examples, the speed of the rotating portion and the beam width are controlled to maintain a constant pitch P as the subject support speed changes according to the linear motion pattern. Suitable methods for determining the pitch P, and suitable values for P, have been previously described.

In some examples, rather than controlling the one or more parameters of the computed tomography scanner responsive to subject support speed to maintain a constant pitch (as previously described), the one or more parameters may be controlled to maintain a constant irradiation per unit volume of the examination region (i.e. a constant dose). An irradiation per unit volume of the examination region is functionally equivalent to a total radiation dosage per volume of a subject positioned on the subject support.

A measure of total irradiation per unit volume Ir(t) may be defined by the following equation:

$$Ir(t) = \frac{In(t)}{P(t)} \quad (3)$$

where In(t) is radiation (intensity) output by the radiation outputting system and P(t) is the pitch.

Thus, by controlling a pitch (using the beam width and optionally the rotation speed) and optionally an intensity of radiation output by the radiation outputting system, a total irradiation per unit volume of the examination region can be controlled. In particular examples, a total irradiation per unit volume of the examination region can be kept constant for different speeds of the subject support.

The desired value for Ir(t) may be predetermined, e.g. according to some medical protocol or clinical/environmental recommendation (such as those set out in guidelines for CT scanning). In another example, the desired value for Ir(t) may be chosen by a clinician, e.g. employing their experience to choose a suitable level for Ir(t).

Thus, in some embodiments, step 230 comprises controlling the beam width and either the intensity of radiation output by the radiation outputting system or the rotation speed of the rotating portion or both. Thus, a hybrid system for delivering constant dose during a scanning procedure (including an acceleration and/or deceleration phase) may be employed.

In embodiments in which the pitch is kept constant, the radiation output by the radiation outputting system may also be kept constant (i.e. there is no need to change the magnitude of radiation output by the radiation outputting system).

Of course, it will be appreciated that hardware or software limitations may be unable to maintain a constant pitch and/or dosage using approaches previously described. However, a change in pitch and/or dosage could be minimized by controlling the aforementioned parameters to the best of the systems capabilities to reduce an impact on a subject.

Thus, rather than attempting to maintain a constant pitch, controlling the one or more parameters of the computer tomography scanner (including at least a beam width) may be used to reduce a range of (i.e. reduce a change in) pitch and/or total/average irradiation per unit volume of the examination region.

For the sake of completeness, it is noted that other parameters and functions of the scanning procedure may be controlled according to well-known CT scanning protocols, e.g. control of sampling speeds, operation of radiation measurement system functionality and so on. The present disclosure proposes approaches for modifying some (i.e. not necessarily all) aspects of the scanning procedure.

In some examples, the step 230 of controlling one or more parameters of the computed tomography scanner comprises setting and maintaining the beam width to be equal to 0 until the radiation generated by the radiation source has stabilized.

Thus, step 210 may comprise controlling a radiation source to begin emitting radiation, and step 230 may comprise controlling the beam width to remain at 0 until the radiation source has stabilized (i.e. emitted radiation is near-constant). This reduces unnecessary irradiation of the subject, thereby reducing radiation dosage. Once the radiation source has stabilized, the beam width may be controlled accordingly to previously described approaches, i.e. responsive to the speed of the subject support.

In some further examples, step 220 may comprise not beginning a linear movement of the subject support, i.e. keeping the subject support stationary, until the radiation source has stabilized. This ensures that the size of an imaging area of the subject is maintained or increased.

Mechanisms for identifying when the radiation source has stabilized will be readily apparent to the skilled person, e.g. by waiting a predetermined period of time after powering the radiation source (e.g. according to known times for the radiation source to stabilize).

Thus, there may effectively be a delay between steps 210 and the performance of steps 220 and 230 (during which time the beam width is maintained or kept at 0 or near-zero), to allow the radiation source to stabilize.

Previous embodiments have described how a beam width is controlled, during a scanning procedure, responsive to a speed of a subject support. One method of controlling a beam width is to control the operation of the radiation outputting system.

In particular, where the radiation outputting system comprises a radiation source and a collimator, an operation of the collimator may be controlled to define the beam width. For instance, a size of a collimator opening may be controlled to control the beam width, e.g. a width of a collimator opening.

Figure 4:
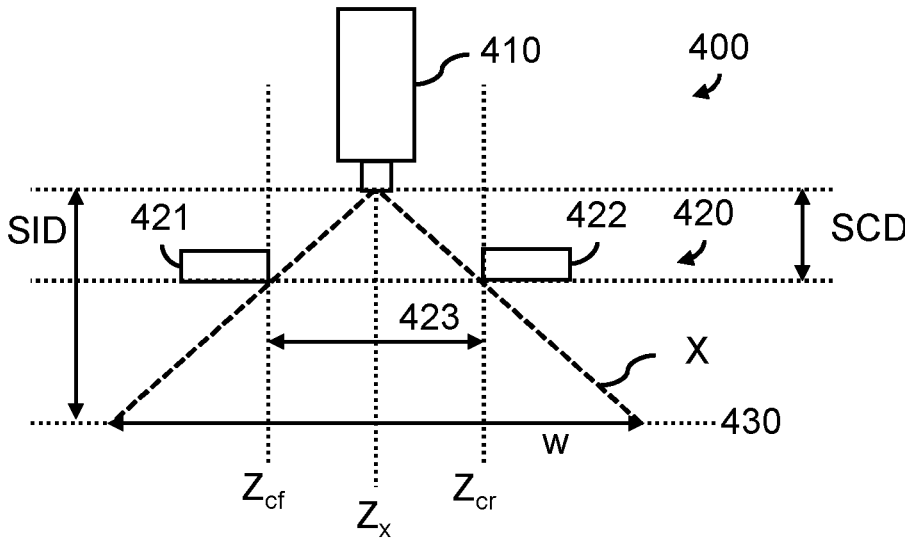
FIG. 4 illustrates a radiation outputting system.

FIG. 4 illustrates one example of a radiation outputting system 400 for use with an embodiment of the invention.

The radiation outputting system 400 comprises a radiation source 410 that outputs a beam X of radiation (e.g. an X-ray source such as an X-ray tube) and a collimator 420. The collimator 420 is formed of a front blade 421 and a rear blade 422. The front 421 and rear 422 blades are aligned in a direction of travel of the subject support (i.e. along a z-axis). In particular, during a positive travel direction of the subject support, the front blade leads the rear blade, i.e. is positioned ahead of the rear blade. The collimator opening 423 is the gap formed between the front 421 and rear 422 blades. Any radiation output by the radiation source 410 that falls on the front or rear blades (i.e. and not in the collimator opening) is blocked (and not illustrated for the sake of clarity). The position of the front 421 and rear 422 blades can be individually controlled in order to control the size of the collimator opening (and therefore the size of the beam width).

The size C of the collimator opening 423 at time t can be calculated using the following equation:

$$C(t) = \frac{w(t) \cdot SCD}{SID} \quad (4)$$

where w(t) is the (desired) beam width at time t, SCD is the distance from the radiation source 410 to the collimator opening and SID is the distance from the radiation source 410 to the isocenter 430 of the computed tomography scanner. SCD and SID can be predetermined or known values (e.g. according to the structure of the computed tomography scanner).

The position of the front and rear blade edges can be defined based on a position $Z_X(t)$ of the center of the X-ray beam during the course of the scanning procedure. The position ($Z_{cf}$) of the collimator edge of the front blade 421 will be equal to $Z_X(t)+0.5C(t)$. The position ($Z_{cr}$) of the collimator edge of the rear blade 422 will be equal to $Z_X(t)-0.5C(t)$.

In one scenario, a linear motion of the table follows a linear motion pattern being a sequence of an acceleration phase (of constant acceleration), a steady state phase, and a deceleration phase (of constant deceleration). In this scenario, for any time t, the center of the X-ray beam $Z_X(t)$ (along the z-axis) relative to the starting point of the subject support position (along the z-axis) can be defined as.

$$Z_X(t) = \begin{cases} \frac{1}{2}a \cdot t^2 & t \leq t_1 \\ \frac{1}{2}a \cdot t_1^2 + v_{max}(t-t_1) & t_1 \leq t \leq t_2 \\ \frac{1}{2}a \cdot t_1^2 + v_{max}(t2-t_1) \mp \frac{1}{2}d(t-t_2)^2 & t \geq t_2 \end{cases} \quad (5)$$

where:

t: time during the scanning procedure, starting from to a: subject support acceleration d: subject support deceleration $V_{max}$: maximum subject support speed during steady state $t_1$: time acceleration phase ends $t_2$: time deceleration phase starts $Z_X(0)$ or $Z_X(t_0)$ is defined as the starting position of the center of the X-ray beam, which here defines a point 0 on the z-axis.

Other approaches for determining the position of the center of the X-ray beam will be apparent to the skilled person, e.g. depending upon the linear motion pattern employed when moving the subject support. In particular, the skilled person would be readily capable of combining various equations of motion (as illustrated with equation (5)) in order to predict or determine the position $Z_X(t)$ of the center of the X-ray beam with respect to time.

Figure 5:
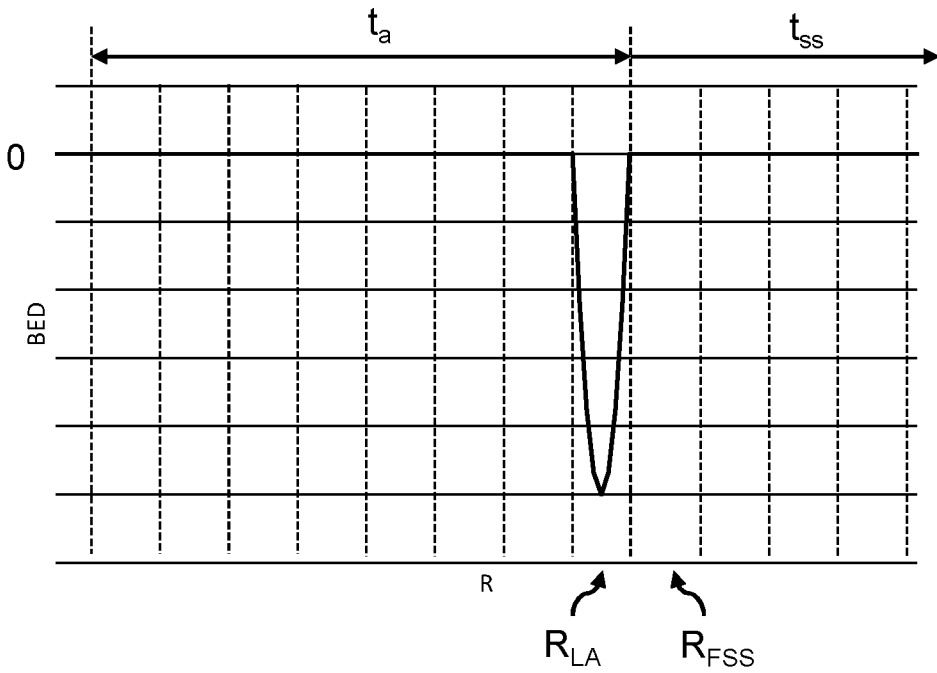
FIG. 5 illustrates a relationship between a beam edge difference and a rotation of a rotating portion.

FIG. 5 illustrates an example beam edge difference (BED) with respect to rotation angle (R) at a transition between an acceleration phase $t_a$ and a steady state phase $t_{ss}$—in which the collimator opening size alone is controlled to maintain a pitch at a constant value of 1. Vertical dashed lines represent completion of one full rotation (i.e. there is a $2\pi$ rad difference between each vertical dashed line).

The beam edge difference BED is a difference between the instant position of the beam front edge (i.e. after a rotation of N radians of the rotating portion) and the instant position of the beam rear edge at the same rotation angle in the next full rotation (i.e. after a rotation of N+2π radians of the rotating portion). The beam edge difference BED therefore effectively represents a measure of overlap between a first beam after N rotations and a second beam after N+1 rotations of the rotating portion.

It can be seen that there is a non-zero BED in the last rotation $R_{LA}$ during the acceleration phase, in which the size of the collimator opening is still increasing during this last rotation, but is kept constant in the next rotation $R_{FSS}$ (the first rotation in the steady state phase). However, it is noted that the BED is small compared to the collimator opening size, so can be considered negligible.

A similar BED can also be found for the rear edge of the beam in the first rotation. In the first rotation, ideally the rear edge of the beam shall be at position 0 but, in practice, there is small (≤1.0 mm) difference to 0. This is due to errors that can arise when trying to match a fixed position for the starting edge using a moving blade.

If desired, the non-zero BEDs can be compensated. To compensate the first identified non-zero BED (illustrated in FIG. 5), the front beam edge of the last rotation in the acceleration phase can be set as the corresponding rear beam edge of the first rotation of the steady state phase.

To compensate the second identified non-zero BED (not illustrated) the rear beam edge position can be set at 0 in the first rotation.

Figure 6:
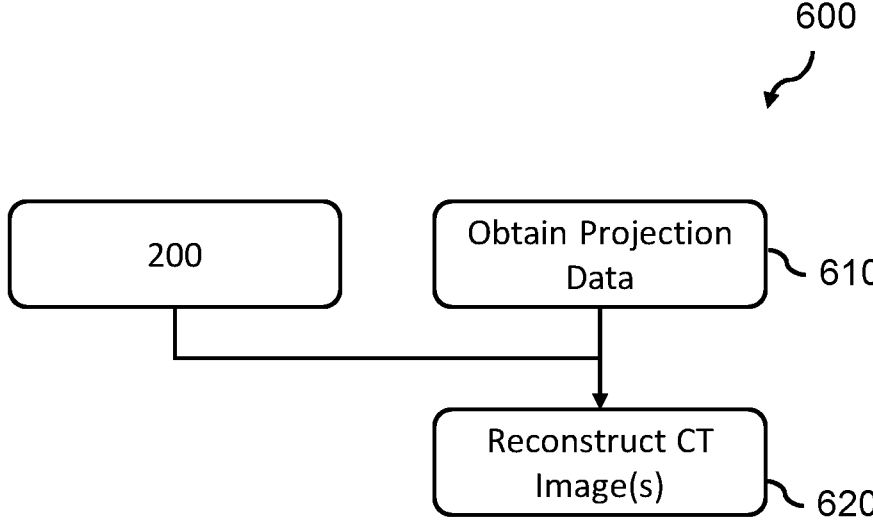
FIG. 6 illustrates a method according to an embodiment.

FIG. 6 illustrates a method 600 according to an embodiment.

The method 600 comprises the method 200 (previously described) as well as a step 610 of obtaining, using a radiation measurement system mounted on the rotating portion, raw signal data (i.e. projection data) responsive to the absorption of radiation output by the radiation outputting system by a subject positioned on the subject support.

A typical radiation measurement system may be formed of an array of discrete radiation detection elements, each of which contributes to the raw signal data generated by the radiation measurement system. These discrete radiation detection elements may be arranged in a grid of rows (aligned in the direction of the z-axis, i.e. the direction of travel of the subject support) and columns.

The method may further comprise a step 620 of processing the raw signal data (projection data) to reconstruct one or more CT images from the raw signal data. The CT image(s) may comprise one or more 2D CT images and/or one or more 3D CT images.

Mechanisms for obtaining raw signal data (projection data) and reconstructing CT images from raw signal data are well known in the art.

Processes for performing steps 610 and 620 typically comprise iteratively sampling an amount of radiation incident on the radiation measurement system.

Figure 7:
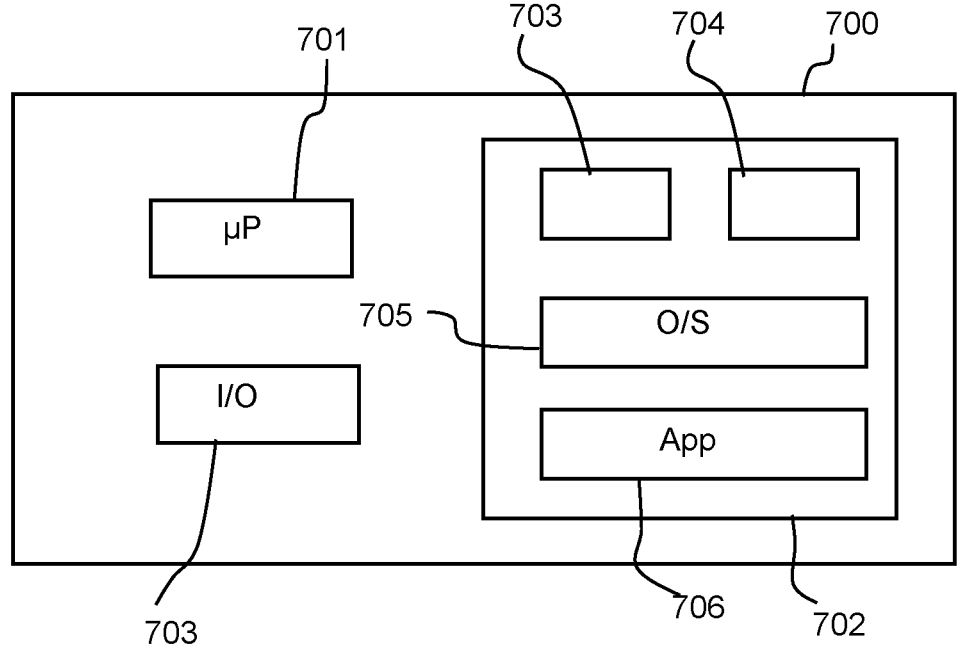
FIG. 7 illustrates a processing system according to an embodiment.

By way of further example, FIG. 7 illustrates an example of a processing system 700 within which one or more parts of an embodiment may be employed. The processing system 700 provides one example of a processing system 118 described with reference to FIG. 1.

Various operations discussed above may utilize the capabilities of the processing system 700. For example, one or more parts of a mechanism for controlling the operation of a computed tomography scanner may be incorporated in any element, module, application, and/or component discussed herein. In this regard, it is to be understood that system functional blocks can run on a single computer or may be distributed over several computers and locations (e.g. connected via Ethernet and/or fieldbus or the internet).

The processing system 700 includes, but is not limited to, PCs, workstations, laptops, PDAs, palm devices, servers, storages, and the like. Generally, in terms of hardware architecture, the processing system 700 may include one or more processors 701, memory 702, and one or more I/O devices 707 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 701 is a hardware device for executing software that can be stored in the memory 702. The processor 701 can be virtually any custom made or commercially available processor, a central processing unit (CPU), a digital signal processor (DSP), or an auxiliary processor among several processors associated with the processing system 700, and the processor 701 may be a semiconductor based microprocessor (in the form of a microchip) or a microprocessor.

The memory 702 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM). electronically erasable programmable read only memory (EEPROM), programmable read only memory (PROM), tape, compact disc read only memory (CD-ROM), disk, diskette, cartridge, cassette or the like, etc.). Moreover, the memory 702 may incorporate electronic, magnetic, optical, and/or other types of storage media. Note that the memory 702 can have a distributed architecture, where various components are situated remote from one another, but can be accessed by the processor 701.

The software in the memory 702 may include one or more separate programs, each of which comprises an ordered listing of executable instructions for implementing logical functions. The software in the memory 702 includes a suitable operating system (O/S) 705, compiler 704, source code 703, and one or more applications 706 in accordance with exemplary embodiments. As illustrated, the application 706 comprises numerous functional components for implementing the features and operations of the exemplary embodiments. The application 706 of the processing system 700 may represent various applications, computational units, logic, functional units, processes, operations, virtual entities, and/or modules in accordance with exemplary embodiments, but the application 706 is not meant to be a limitation.

The operating system 705 controls the execution of other computer programs, and provides scheduling, input-output control, file and data management, memory management, and communication control and related services. It is contemplated by the inventors that the application 706 for implementing exemplary embodiments may be applicable on all commercially available operating systems.

Application 706 may be a source program, executable program (object code), script, or any other entity comprising a set of instructions to be performed. When the application 706 is a source program, then the program is usually translated via a compiler (such as the compiler 704), assembler, interpreter, or the like, which may or may not be included within the memory 702, so as to operate properly in connection with the O/S 705. Furthermore, the application 706 can be written as an object oriented programming language, which has classes of data and methods, or a procedure programming language, which has routines, subroutines, and/or functions, for example but not limited to, C, C++, C #, Pascal, BASIC, API calls, HTML, XHTML, XML, ASP scripts, JavaScript, FORTRAN, COBOL, Perl, Java, ADA, .NET, and the like.

The I/O devices 707 may include input devices such as, for example but not limited to, a mouse, keyboard, scanner, microphone, camera, etc. Furthermore, the I/O devices 707 may also include output devices, for example but not limited to a printer, display, etc. Finally, the I/O devices 707 may further include devices that communicate both inputs and outputs, for instance but not limited to, a network interface card (NIC) or modulator/demodulator (for accessing remote devices, other files, devices, systems, or a network), a radio frequency (RF) or other transceiver, a telephonic interface, a bridge, a router, etc. The I/O devices 707 also include components for communicating over various networks, such as the Internet or intranet.

If the processing system 700 is a PC, workstation, intelligent device or the like, the software in the memory 702 may further include a basic input output system (BIOS) (omitted for simplicity). The BIOS is a set of essential software routines that initialize and test hardware at startup, start the O/S 705, and support the transfer of data among the hardware devices. The BIOS is stored in some type of read-only-memory, such as ROM, PROM, EPROM, EEPROM or the like, so that the BIOS can be executed when the processing system 700 is activated.

When the processing system 700 is in operation, the processor 701 is configured to execute software stored within the memory 702, to communicate data to and from the memory 702, and to generally control operations of the processing system 700 pursuant to the software. The application 706 and the O/S 705 are read, in whole or in part, by the processor 701, perhaps buffered within the processor 701, and then executed.

When the application 706 is implemented in software it should be noted that the application 706 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 706 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The skilled person would be readily capable of developing a processing system for carrying out any herein described method. Thus, each step of the flow chart may represent a different action performed by a processing system, and may be performed by a respective module of the processing system.

Embodiments may therefore make use of a processing system. The processing system can be implemented in numerous ways, with software and/or hardware, to perform the various functions required. A processor is one example of a processing system which employs one or more microprocessors that may be programmed using software (e.g., microcode) to perform the required functions. A processing system may however be implemented with or without employing a processor, and also may be implemented as a combination of dedicated hardware to perform some functions and a processor (e.g., one or more programmed microprocessors and associated circuitry) to perform other functions.

Examples of processing system components that may be employed in various embodiments of the present disclosure include, but are not limited to, conventional microprocessors, application specific integrated circuits (ASICs), and field-programmable gate arrays (FPGAs).

In various implementations, a processor or processing system may be associated with one or more storage media such as volatile and non-volatile computer memory such as RAM, PROM, EPROM, and EEPROM. The storage media may be encoded with one or more programs that, when executed on one or more processors and/or processing systems, perform the required functions. Various storage media may be fixed within a processor or processing system or may be transportable, such that the one or more programs stored thereon can be loaded into a processor or processing system.

It will be understood that disclosed methods are preferably computer-implemented methods. As such, there is also proposed the concept of a computer program comprising code means for implementing any described method when said program is run on a processing system, such as a computer. Thus, different portions, lines or blocks of code of a computer program according to an embodiment may be executed by a processing system or computer to perform any herein described method. In some alternative implementations, the functions noted in the block diagram(s) or flow chart(s) may occur out of the order noted in the figures. For example, two blocks shown in succession may, in fact, be executed substantially concurrently, or the blocks may sometimes be executed in the reverse order, depending upon the functionality involved.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A computer-implemented method of operating a computed tomography (CT) scanner, comprising:
  providing a subject support configured to move linearly;
  providing a rotating portion of the CT scanner that mounts a radiation outputting source and controllably rotates around the subject support;
  controlling the radiation outputting source to output radiation during an imaging phase of the scanning procedure;
  controlling the subject support to move linearly, the linear movement of the subject support during the imaging phase of the scanning procedure including at least one acceleration phase or deceleration phase; and
  controlling one or more parameters of the CT scanner responsive to the speed of the subject support, wherein the one or more parameters comprises at least a beam width of the radiation output by the radiation outputting source, and wherein controlling the one or more parameters comprises controlling the beam width proportionally to the speed of the subject support.

2. The computer-implemented method of claim 1, wherein:
  the radiation outputting source comprises a radiation source configured to generate radiation and a collimator configured to control the beam width of radiation generated by the radiation source; and
  controlling the one or more parameters of the CT scanner comprises controlling the beam width by controlling an operation of the collimator.

3. The computer-implemented method of claim 2, wherein the collimator comprises a collimator opening having a controllable width, and controlling the beam width comprises controlling a width of the collimator opening responsive to the speed of the subject support.

4. The computer-implemented method of claim 3, wherein the width of the collimator opening is defined by a distance between a front blade and a rear blade aligned in a direction of travel of the subject support, and controlling a width of the collimator opening comprises controlling the distance between the front blade and the rear blade.

5. The computer-implemented method of claim 1, wherein controlling one or more parameters of the CT scanner comprises setting and maintaining the beam width to be substantially equal to 0 until the radiation generated by the radiation outputting source has stabilized.

6. The computer-implemented method of claim 1, wherein controlling the one or more parameters of the CT scanner comprises controlling the one or more parameters such that a total radiation dosage per volume of a subject positioned on the subject support remains substantially constant throughout the scanning procedure.

7. The computer-implemented method of claim 1, wherein controlling one or more parameters of the CT scanner comprises:
  controlling the one or more parameters of the CT scanner so that a CT scan pitch is constant throughout the scanning procedure; and/or
  controlling the beam width to be equal to the product of the speed of the subject support and the time taken for the rotating portion to perform a $2\pi$ rotation, divided by a desired CT scan pitch.

8. The computer-implemented method of claim 1, wherein the one or more parameters of the CT scanner further comprises an intensity of the radiation output by the radiation outputting source.

9. The computer-implemented method of claim 1, wherein the one or more parameters of the CT scanner further comprises a rotation speed of the rotating portion of the CT scanner.

10. The computer-implemented method of claim 1, wherein controlling the subject support to move linearly comprises controlling the subject support, during the imaging phase, to have a linear movement including a single acceleration and/or a single deceleration phase.

11. The computer-implemented method of claim 1, wherein the scanning procedure comprises obtaining, using a radiation measurement system mounted on the rotating portion, raw signal data responsive to the absorption of radiation output by the radiation outputting source by a subject positioned on the subject support.

12. An imaging system, comprising:

a radiation detector; and a computed tomography (CT) scanner comprising a subject support configured to move linearly and a rotating portion that mounts a radiation outputting source and controllably rotates around the subject support, wherein the CT scanner is configured to:

control the radiation outputting source to output radiation during an imaging phase of the scanning procedure;

control the subject support to move linearly, the linear movement of the subject support during the imaging phase of the scanning procedure including at least one acceleration or deceleration phase; and control one or more parameters of the CT scanner responsive to the speed of the subject support, wherein the one or more parameters comprises at least a beam width of the radiation output by the radiation outputting source, and wherein controlling the one or more parameters comprises controlling the beam width proportionally to the speed of the subject support.

13. A non-transitory computer-readable medium for storing executable instructions, which cause a method for operating a computed tomography (CT) scanner to be performed, the method comprising:

providing a subject support configured to move linearly;

providing a rotating portion of the CT scanner that mounts a radiation outputting source and controllably rotates around the subject support;

controlling the radiation outputting source to output radiation during an imaging phase of the scanning procedure;

controlling the subject support to move linearly, the linear movement of the subject support during the imaging phase of the scanning procedure including at least one acceleration phase or deceleration phase; and controlling one or more parameters of the CT scanner responsive to the speed of the subject support, wherein the one or more parameters comprises at least a beam width of the radiation output by the radiation outputting source, and wherein controlling the one or more parameters comprises controlling the beam width proportionally to the speed of the subject support.

* * * * *